United States Patent
Tamaki et al.

(10) Patent No.: US 8,974,561 B2
(45) Date of Patent: Mar. 10, 2015

(54) MANUFACTURING METHOD OF GLASS SUBSTRATE FOR MAGNETIC DISK, MAGNETIC DISK, AND MAGNETIC RECORDING / REPRODUCING DEVICE

(71) Applicant: Hoya Corporation, Tokyo (JP)

(72) Inventors: Masanori Tamaki, Higashimurayama (JP); Hiroki Nakagawa, Hokuto (JP); Yoshihiro Tawara, Hirasaki (JP)

(73) Assignee: Hoya Corporation, Tokyo (JP)

( * ) Notice: Subject to any disclaimer, the term of this patent is extended or adjusted under 35 U.S.C. 154(b) by 49 days.

(21) Appl. No.: 13/627,057

(22) Filed: Sep. 26, 2012

(65) Prior Publication Data

US 2013/0083425 A1    Apr. 4, 2013

(30) Foreign Application Priority Data

Sep. 30, 2011  (JP) ................................. 2011-218624
Sep. 30, 2011  (JP) ................................. 2011-218659

(51) Int. Cl.
| | | |
|---|---|---|
| *G11B 5/73* | (2006.01) | |
| *C03C 21/00* | (2006.01) | |
| *G11B 5/84* | (2006.01) | |
| *C03C 19/00* | (2006.01) | |
| *C09G 1/02* | (2006.01) | |
| *B24D 3/00* | (2006.01) | |
| *A61C 17/00* | (2006.01) | |

(52) U.S. Cl.
CPC .............. *G11B 5/8404* (2013.01); *C03C 19/00* (2013.01); *C09G 1/02* (2013.01); *C03C 21/008* (2013.01); *A61C 17/00* (2013.01); *B24D 3/005* (2013.01)

USPC .................. 51/307; 51/295; 51/308; 51/309; 516/98; 438/691; 438/692; 438/693; 428/846.9; 428/848.8

(58) Field of Classification Search
CPC ...... C03C 21/008; C03C 19/00; B24D 3/005; C09G 1/02; A61C 17/00; G11B 5/8404
USPC ....................... 51/307, 308, 309, 295; 516/98; 438/691, 692, 693; 428/846.9, 848.8
See application file for complete search history.

(56) References Cited

U.S. PATENT DOCUMENTS

| | | | |
|---|---|---|---|
| 6,451,696 B1 * | 9/2002 | Hara et al. ..................... | 438/691 |
| 8,778,212 B2 * | 7/2014 | Jin et al. ........................... | 216/89 |
| 2003/0005647 A1 * | 1/2003 | Towery et al. .................. | 51/308 |
| 2005/0028449 A1 * | 2/2005 | Miyata et al. ................... | 51/308 |
| 2008/0168717 A1 * | 7/2008 | Can et al. ........................ | 51/295 |
| 2008/0305943 A1 * | 12/2008 | Davidson et al. .............. | 501/103 |
| 2009/0105354 A1 * | 4/2009 | Oswald et al. .................. | 516/98 |
| 2013/0109194 A1 * | 5/2013 | Shirota et al. ................. | 438/759 |

FOREIGN PATENT DOCUMENTS

JP    2783329 B    5/1998

* cited by examiner

*Primary Examiner* — Kevin M. Bernatz
(74) *Attorney, Agent, or Firm* — Global IP Counselors, LLP

(57) ABSTRACT

A manufacturing method of a glass substrate for a magnetic disk is provided whereby nano pits and/or nano scratches cannot be easily produced in polishing a principal face of a glass substrate using a slurry containing zirconium oxide as an abrasive. The manufacturing method of a glass substrate for a magnetic disk includes, for instance, a polishing step of polishing a principal face of a glass substrate using a slurry containing, as an abrasive, zirconium oxide abrasive grains having monoclinic crystalline structures (M) and tetragonal crystalline structures (T).

13 Claims, 4 Drawing Sheets

ROLL-OFF SHAPE

SKI JUMP SHAPE

MANUFACTURING METHOD OF GLASS SUBSTRATE FOR MAGNETIC DISK, MAGNETIC DISK, AND MAGNETIC RECORDING / REPRODUCING DEVICE

CROSS-REFERENCE TO RELATED APPLICATION

This application claims priority to Japanese Patent Application No. 2011-218659, filed on Sep. 30, 2011, and Japanese Patent Application No. 2011-218624, filed on Sep. 30, 2011, the entirety of which is hereby incorporated by reference in its entirety.

FIELD

The present invention relates to a manufacturing method of a glass substrate for a magnetic disk.

BACKGROUND

A variety of devices, including PCs (Personal Computers) and DVD (Digital Versatile Disc) recorders, have been recently embedded with a HDD (Hard Disk Drive) for data recording. The HDDs, used for portably designed machines such as laptop PCs, are provided with a magnetic disk formed by a glass substrate with a magnetic layer disposed thereon. The HDDs are configured to record/reproduce magnetic recording information in/out of the magnetic layer using a magnetic head floated slightly above the magnetic disk face. Glass substrates have been preferably used as the substrates for the magnetic disks due to less plastically deformable characteristic thereof compared to metal substrates (e.g., aluminum substrates) and so forth.

Meanwhile, development of high-density magnetic recording has been underway for meeting the demand of increase in storage volume of HDDs. For example, the magnetic recording information area (recording bit) is minutely divided by means of a perpendicular magnetic recording method for perpendicularly directing a magnetization direction in the magnetic layer with respect to the substrate face. Accordingly, the recording volume can be increased in a single disk substrate. Further, enhancement of accuracy in information recording/reproducing (i.e., enhancement of an S/N ratio) has been underway by further protruding a recording/reproducing element of the magnetic head and thereby reducing distance between the magnetic head and the magnetic recording layer in order to further increase the storage volume. It should be noted that a control mechanism of the recording/reproducing element of the magnetic head described above is referred to as a DFH (Dynamic Flying Height) control mechanism and the magnetic head embedded with the control mechanism is referred to as a DFH head. A substrate for a magnetic disk to be used for a HDD in combination with such DFH head is fabricated to have an extremely small surface asperity for avoiding collision or contact with the magnetic head and the recording/reproducing element protruded therefrom.

Steps of fabricating a glass substrate for a magnetic disk include: a grinding step of executing grinding using fixed abrasive grains with respect to a principal face of a glass blank formed in a flat plate shape after press-molding; and a polishing step of executing polishing with respect to the principal face for removing flaws and distortion left on the principal face due to the grinding step. In the aforementioned polishing step with respect to the principal face, a method of using zirconium oxide (zirconia) abrasive grains as an abrasive has been conventionally known (Japan Patent No. 2783329).

CITATION LIST

Patent Literature

Patent Literature 1: Japan Patent No. 2783329

SUMMARY OF THE INVENTION

Technical Problem

Incidentally, Japan Patent No. 2783329 discloses measurement of the surface shape of a principal face of a glass substrate by a probe type profilometer. However, so-called nano pits or nano scratches, which have been problematic in recent years, cannot be measured by such probe type measuring method. A nano pit is a recess produced on a principal face of a glass substrate and has a nano-level size, for instance, Rv of 50 nm or less. It should be noted that Rv herein refers to a depth from a surface with average roughness when measurement is conducted using AFM (Atomic Force Microscope). On the other hand, a nano scratch is a scratch produced on a principal face of a glass substrate and has nano-level width and depth. Such recess or scratch of minute size has not been conventionally problematic. However, in recent years, the magnetic recording information has been highly integrated and recording density has been thereby increased in the premise of recording and reproducing with a DFH head. With such trend, it has been increasingly important to reduce the number of nano pits and/or nano scratches on a principal face of a glass substrate for a magnetic disk. In short, an individual recording bit in which information is recorded has been further miniaturized in its size than ever before. As a result, a nano-level scratch or etc., having not been conventionally problematic, has come to account for a relatively substantial fraction of a recording bit in terms of its size. It has been thereby revealed that an S/N (Signal to Noise) ratio is reduced in recording/reproducing in/out of a recording bit containing nano pits and/or nano scratches and a recording/reproducing error is accordingly produced. Thus, it has been increasingly important to reduce the level of nano pits and/or nano scratches on a principal face of a glass substrate for a magnetic disk.

Further, to implement 500 GB per a magnetic disk of 2.5 inch (a diameter of 65 mm), it is presumed that a track density of roughly 350 kTPI (Track Per Inch) or greater and a linear recording density of roughly 1700 kBPI (Bits Per Inch) or greater are required and the size of 1 bit is required to be reduced to 15 nm×70 nm or less, for instance. As a result of such enhancement in recording density and remarkable reduction in size of 1 bit, an area (or volume) occupied by a deficit in 1 bit is relatively increased even when the deficit is a nano-size deficit (e.g., a nano pit or a nano scratch) that has not been conventionally problematic. Therefore, degradation in magnetic signal quality (e.g., S/N ratio) has been unable to be ignored.

It should be noted that nano pits and/or nano scratches, produced in a polishing step (hereinafter arbitrarily referred to as "a first polishing step") with respect to principal faces of a glass substrate using zirconium oxide as an abrasive, can be removed by a post polishing step (hereinafter arbitrarily referred to as "a second polishing step") using colloidal silica and etc. as an abrasive. However, when a removal stock is herein too large, a trouble (rounded edge) tends to be produced, including a trouble that an edge of a principal face of a glass substrate is formed in a roll-off shape. Further, when a chemically strengthening step of forming a compression stress layer on each principal face of a glass substrate is executed between the first polishing step and the second polishing step, difference in thickness is more easily produced between the compression stress layers on the both principal faces of the glass substrate in proportion to increase in the removal stock in the second polishing step to be executed after the chemically strengthening step. When difference in thickness is produced between the compression stress layers on the both principal faces, degradation in strength is caused on the principal face having thereon a thinner compression stress layer and degradation in surface asperity (e.g., deflection) is caused on a principal face due to difference in compression stress between the both principal faces. Therefore, it is required to prevent deep nano pits and/or deep nano scratches from being formed in the first polishing step so that the removal stock can be inhibited (to be roughly 5 μm or less, for instance) in polishing of the second polishing step.

From the aforementioned perspectives, it is preferable to prevent a flaw such as a deep nano pit or a deep nano scratch from being easily produced and to prevent an edge of a principal face of a glass substrate from being easily rounded in polishing the principal face of the glass substrate using a shiny containing zirconium oxide as an abrasive.

Further, from another perspective, it has been demanded to enhance the polishing speed for enhancing productivity than ever before in polishing a principal face of a glass substrate using a slurry containing zirconium oxide as an abrasive.

In view of the above, it is an object of a first aspect of the present invention to provide a manufacturing method of a glass substrate for a magnetic disk whereby a flaw such as a deep nano scratch can be prevented from being easily produced on a principal face of the glass substrate in polishing the principal face of the glass substrate using a slurry containing zirconium oxide as an abrasive.

It is an object of another aspect of the present invention to provide a manufacturing method of a glass substrate for a magnetic disk whereby a good polishing speed can be reliably achieved and an edge of a principal face of the glass substrate can be prevented from being easily rounded.

Solution to Problem

It is generally known that the crystalline structures of zirconium oxide (also referred to as zirconia) are changed into: monoclinic crystalline structures at a temperature of roughly 1,100 degrees Celsius or less; tetragonal crystalline structures at a temperature roughly in a range of 1,100 to 2,370 degrees Celsius; and cubic crystalline structures at a temperature of roughly 2,370 degrees Celsius or greater. It should be noted that, even when zirconium oxide of the monoclinic crystalline structures is heated to a higher temperature and is phase-transited to the tetragonal crystalline structures, it is recognized that the phase-transited zirconium oxide is again phase-transited and returned to the monoclinic crystalline structures by cooling it down to the room temperature. Further, when solid-soluted with rare-earth oxide (e.g., calcium oxide, magnesium oxide or yttrium oxide) as a stabilizing agent, zirconium oxide is changed, even at the room temperature, into stabilized or partially stabilized zirconia that reaches a stable or metastable state in the form of the tetragonal crystalline structures.

Further, the inventors of the present invention obtained the following findings with respect to the aforementioned objects as a result of dedicated research focused on the crystalline structures of zirconium oxide contained as an abrasive in a slurry.

Zirconium oxide, formed only by the monoclinic crystalline structures, has a low-level hardness. Therefore, when a principal face of a glass substrate is polished using abrasive grains of zirconium oxide as an abrasive, the abrasive grains are fractured during polishing. The number of abrasive grains with small particle sizes is herein increased in zirconium oxide by the fracturing of the abrasive grains, and a particle size distribution is extended to a lower particle size side. Accordingly, a rate of abrasive grains with relatively large particle sizes is reduced, and the principal face of the glass substrate is polished while the load applied to a polisher platen locally acts on the abrasive grains with relatively large particle sizes without dispersedly acting on a large number of abrasive grains. Therefore, nano pits and/or nano scratches are easily produced on the principal face of the glass substrate.

On the other hand, stabilized or partially stabilized zirconium oxide, formed only by the tetragonal crystalline structures, has a hardness extremely higher than that of a glass as a processing target. Therefore, the abrasive grains are not fractured in the stabilized or partially stabilized zirconium oxide, and thereby, nano pits and/or nano scratches are easily produced on the principal face of the glass substrate when a load locally acts on the abrasive grains. In other words, zirconium oxide has hardness suitable for executing polishing of the principal face of the glass substrate.

In view of the above, the inventors of the present invention found that an appropriate hardness of zirconium oxide for polishing a principal face of a glass substrate can be obtained by preparing zirconium oxide abrasive grains formed by both of the monoclinic crystalline structures and the tetragonal crystalline structures. In other words, nano pits and/or nano scratches are not easily produced on a principal face of a glass substrate by polishing the principal face of the glass substrate using, as an abrasive, a slurry that contains zirconium oxide abrasive grains formed by both of the monoclinic crystalline structures and the tetragonal crystalline structures. Zirconium oxide formed by such crystalline structures can be obtained by sintering zirconium oxide formed by the monoclinic crystalline structures roughly at a temperature under which phase transition from the monoclinic crystalline structures to the tetragonal crystalline structures begins.

Based on the above, a first aspect of the present invention relates to a manufacturing method of a glass substrate for a magnetic disk including a polishing step of polishing a principal face of the glass substrate using a slurry containing zirconium oxide abrasive grains having monoclinic crystalline structures and tetragonal crystalline structures as an abrasive.

In the aforementioned manufacturing method of a glass substrate for a magnetic disk according to the first aspect, in the zirconium oxide abrasive grains, a ratio of the amount of the tetragonal crystalline structures with respect to the amount of the monoclinic crystalline structures may preferably fall in a range of 0.7 to 3.0%. It should be noted that the ratio is obtained by means of x-ray diffraction and is defined as a ratio of a peak intensity of the tetragonal crystalline structures with respect to a peak intensity of the monoclinic crystalline structures. The peak intensity is herein defined as an integrated peak intensity.

In the aforementioned manufacturing method of a glass substrate for a magnetic disk according to the first aspect, the zirconium oxide abrasive grains may be made of aggregates of primary particles of zirconium oxide and the primary particles of zirconium oxide may have both the monoclinic crystalline structures and the tetragonal crystalline structures.

In the aforementioned manufacturing method of a glass substrate for a magnetic disk according to the first aspect, the zirconium oxide abrasive grains may not contain stabilizing agent.

Further, the inventors of the present invention encountered the aforementioned objects and conducted dedicated research for, as an abrasive, partially stabilized zirconia (or simply referred to as stabilized zirconia) that reaches either a stable state or a metastable state in the form of the cubic crystalline structures even at the room temperature by solid-soluting either a rare-earth element (e.g., calcium oxide, magnesium oxide or yttrium) or its oxide as a stabilizing agent into zirconium oxide. As a result, the inventors found that advantageous effects to be described could be achieved by polishing a glass substrate for a magnetic disk using a slurry containing, as an abrasive, partially stabilized zirconia containing yttrium amongst the rear-earth elements or its oxide.

The hardness of yttrium-contained partially stabilized zirconia is higher than that of zirconium oxide formed only by the monoclinic crystalline structures. Therefore, fracturing of abrasive grains is not easily caused during polishing. Consequently, a particle size distribution does not easily vary and deep scratches are not easily produced on a principal face of a glass substrate. Further, in the case of hardness higher than that of zirconium oxide formed only by the monoclinic crystalline structures, physical polishing performance per unit time is enhanced and the polishing speed is also enhanced. Further, it could be assumed that yttrium-contained partially stabilized zirconia attributes to enhancement in polishing speed due to enhancement in its chemical polishing performance with respect to the glass substrate surface. The following could be assumed as the reason for the above. Oxygen deficit is caused in yttrium-contained partially stabilized zirconia, and chemical reactions are accordingly easily caused between zirconium contained in partially stabilized zirconia and oxygen in silicon dioxide ($SiO_2$) in the glass substrate surface. Accordingly, silicon in silicon dioxide is easily separated from the glass substrate surface.

As described above, deep scratches are not easily produced, and thereby, a removal stock is not increased in the post polishing step (i.e., a second polishing step). Therefore, the edge of a principal face of a glass substrate is not easily rounded. Incidentally, the edge of a glass substrate tends to be rounded when abrasive grains are fractured during polishing and the number of minute particles is thereby increased. However, in yttrium-contained partially stabilized zirconia, fracturing of abrasive grains is not easily caused as described above, and therefore, the edge is not easily rounded.

Based on the above, a second aspect of the present invention relates to a manufacturing method of a glass substrate for a magnetic disk including a polishing step of executing polishing using a slurry containing yttrium-contained partially stabilized zirconia as an abrasive.

In the aforementioned manufacturing method of a glass substrate for a magnetic disk according to the second aspect, the abrasive preferably contains yttrium oxide in a range of 1 to 6% by mole.

In the aforementioned manufacturing method of a glass substrate for a magnetic disk according to the second aspect, cubic crystalline structures preferably show the highest peak of diffraction intensity among crystalline structures of zirconia in a diffraction pattern, which is obtained by conducting x-ray powder diffraction for the abrasive, of representing a relation between incident angle and diffraction intensity.

In the aforementioned manufacturing method of a glass substrate for a magnetic disk, the glass substrate is preferably made of glass having the fracture toughness value in a range of 0.4 to 1.5 $MPa \cdot m^{1/2}$.

In the aforementioned manufacturing method of a glass substrate for a magnetic disk, the average particle size D50 of the zirconium oxide abrasive grains is preferably set to be in a range of 0.2 to 0.5 μm.

In the aforementioned manufacturing method of a glass substrate for a magnetic disk, a polisher pad is preferably used for polishing a principal face of the glass substrate in the polishing step, the polisher pad having hardness in a range of 80 to 100 in JIS-A hardness.

The aforementioned manufacturing method of a glass substrate for a magnetic disk may include a post polishing step of polishing using a slimy containing colloidal silica as abrasive grains, which is configured to be executed after the polishing step.

In the aforementioned manufacturing method of a glass substrate for a magnetic disk, a removal stock may be set to be less than or equal to 5 μm in the post polishing step.

The aforementioned manufacturing method of a glass substrate for a magnetic disk may include an intermediate polishing step of polishing using a slurry containing cerium oxide abrasive grains, which is configured to be executed between the polishing step and the post polishing step.

The aforementioned manufacturing method of a glass substrate for a magnetic disk may include a chemically strengthening step configured to be executed between the polishing step and the post polishing step.

A third aspect of the present invention relates to a magnetic disk made of a glass substrate manufactured with the method, in which at least a magnetic layer is formed on a principal face of the glass substrate.

A fourth aspect of the present invention relates to a magnetic recording/reproducing device including the aforementioned magnetic disk and a magnetic head embedded with a DFH (Dynamic Flying Height) control mechanism.

BRIEF DESCRIPTION OF THE DRAWINGS

Referring now to the attached drawings which form a part of this original disclosure.

DESCRIPTION OF THE PREFERRED EMBODIMENTS

Figure 1:
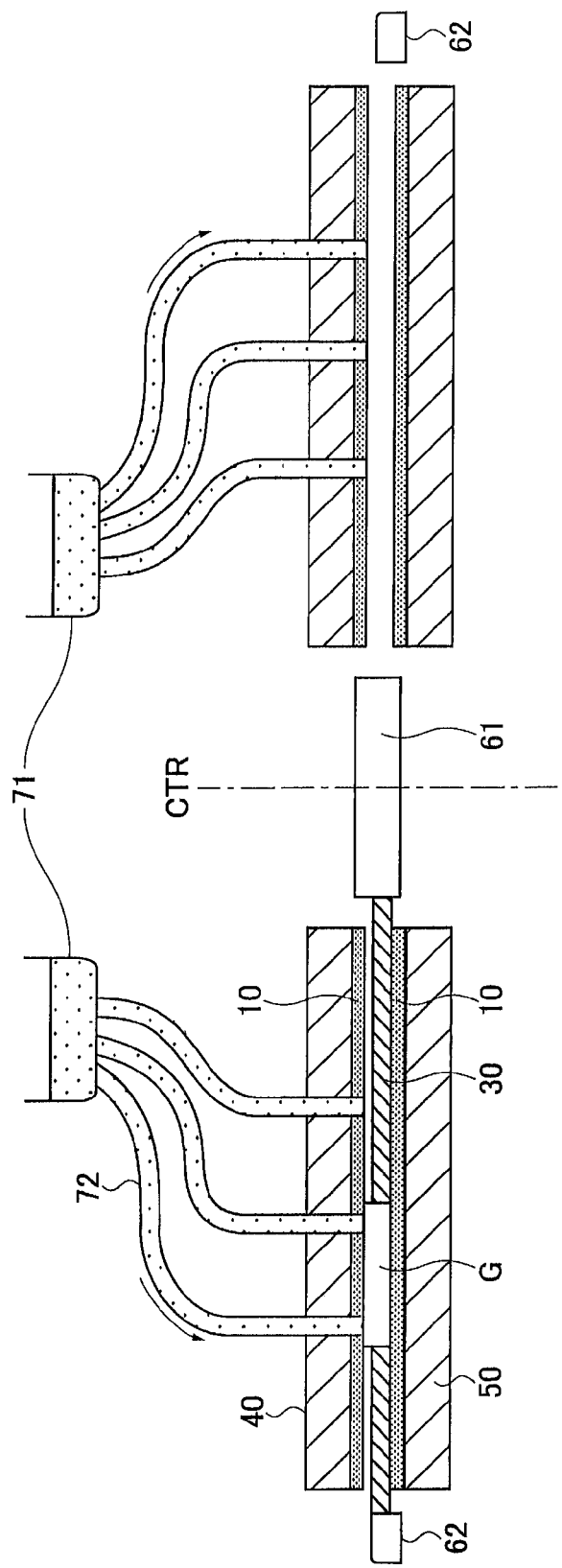
FIG. 1 is a schematic cross-sectional view of a polisher device (double-face polisher device) to be used in a first polishing step.

A manufacturing method of a glass substrate for a magnetic disk according to an exemplary embodiment will be hereinafter explained in detail.
<First Exemplary Embodiment>
(Glass Substrate for Magnetic Disk)

Aluminosilicate glass, soda-lime glass, borosilicate glass or etc. can be used as a material of a glass substrate for a magnetic disk (hereinafter simply referred to as "magnetic disk glass substrate") in the present exemplary embodiment.

Amongst the above, aluminosilicate glass can be preferably used especially in that it can be chemically strengthened and enables fabrication of a magnetic disk glass substrate having better substrate strength and better surface asperity of the principal faces.

The composition of a magnetic disk glass substrate of the present exemplary embodiment is not limited. However, the glass substrate of the present exemplary embodiment is preferably aluminosilicate glass having the oxide-based converted composition of: 50 to 75% by mole of $SiO_2$; 1 to 15% by mole of $Al_2O_3$; totally 5 to 35% by mole of at least one selected from the group of $Li_2O$, $Na_2O$ and $K_2O$; totally 0 to 20% by mole of at least one selected from the group of MgO, CaO, SrO, BaO and ZnO; and totally 0 to 10% by mole of at least one selected from the group of $ZrO_2$, $TiO_2$, $La_2O_3$, $Y_2O_3$, $Ta_2O_5$, $Nb_2O_5$ and $HfO_2$.

The glass substrate of the present exemplary embodiment may be aluminosilicate glass containing, with respect to the entire glass composition, 55 to 75% by mass of $SiO_2$, 5 to 18% by mass of $Al_2O_3$, 3 to 10% by mass of $Li_2O$, 3 to 15% by mass of $Na_2O$, 0 to 5% by mass of $K_2O$, 0 to 5% by mass of MgO, 0.1 to 5% by mass of CaO, and 0 to 8% by mass of $ZrO_2$. Moreover, the glass substrate may be glass which contains neither element of As nor Sb, contains at least one of multivalent elements selected from the group of P, V, Mn, Ni, Nb, Mo, Sn, Ce, Ta, and Bi, and contains at least one or more selected from the group of $Y_2O_3$, $Yb_2O_3$, $La_2O_3$, $Gd_2O_3$, $Nb_2O_5$, $Ta_2O_5$, and $HfO_2$.

In a case where an oxide of the aforementioned multivalent element is $P_2O_5$, $V_2O_5$, $MnO_2$, $Ni_2O_3$, $Nb_2O_5$, $MoO_3$, $SnO_2$, $CeO_2$, $Ta_2O_5$, and $Bi_2O_3$, it is more preferable to set the mole fraction of the total amount of the multivalent element oxide relative to CaO (total amount of the multivalent element oxide divided by CaO) to be greater than or equal to 0.25. Setting the mole fraction as above, air bubbles in the glass can be sufficiently removed.

Furthermore, it is more preferable that the aforementioned multivalent element oxide contains at least one of multivalent elements selected from the group of V, Mn, Sn, and Ce. V, Mn, Sn, and Ce are particularly preferable for removing air bubbles effectively.

As will be described later, in the manufacturing method of a glass substrate for a magnetic disk according to the present exemplary embodiment, a polishing step of polishing a principal face of the glass substrate using a slurry containing zirconium oxide abrasive grains having monoclinic crystalline structures and tetragonal crystalline structures as an abrasive. Hardness of the glass substrate having the aforementioned glass composition is suitable for such the abrasive as above. In other words, the polishing rate can be high while nano pits or nano scratches produced on the principal face of the glass substrate are suppressed in the polishing step.

It should be noted that amorphous aluminosilicate glass is more preferable to be used because the structure of the amorphous aluminosilicate glass is uniform since it has no crystal structure such as crystallized glass. Therefore, the extremely smooth surface can be obtained.

Furthermore, with respect to the glass substrate of the present exemplary embodiment, it is preferable to set the fracture toughness value $K_{1c}$ to be 0.4 to 1.5 [$MPa \cdot m^{1/2}$] in Vickers hardness testing. It is more preferable to set to be 0.5 to 1.0 [$MPa \cdot m^{1/2}$]. When a glass composition having the fracture toughness value in this range is used, nano pits or nano scratches produced on a principal face of the glass substrate can be reduced while the polishing rate is well maintained in the polishing step using the abrasive.

Here, the fracture toughness value $K_{1c}$ can be measured by a method in which a sharp diamond indenter of a well-known Vickers hardness tester is pressed into a glass plate. Specifically, the fracture toughness value $K_{1c}$ can be calculated by the following formula based on the size of an indent which is made when the Vickers diamond indenter is pressed into the glass plate and the length of a crack caused from a corner of the indent. In the formula, P represents a pressing load [N] of the Vickers diamond indenter, a represents half the length of the diagonal line [m] of the Vickers indent, E represents Young's modulus [Pa] of the glass plate, and C represents half the length of a crack.

[Formula 1]

$$K_{1c} = 0.026 \frac{E^{\frac{1}{2}} P^{\frac{1}{2}} a}{C^{\frac{3}{2}}} \quad (1)$$

As recited in WO2012/086664, $K_2O$ has a function of decreasing a fracture toughness value, and $Y_2O_3$, $Yb_2O_3$, $La_2O_3$, $Gd_2O_3$, $Nb_2O_5$, $Ta_2O_5$, and $HfO_2$ are effective components to increase a fracture toughness value. Accordingly, the fracture toughness value of the glass substrate can be controlled by adjusting the amount of these components. In addition, BaO, which is one of alkaline-earth metal oxides, also has a function of decreasing a fracture toughness value.

The magnetic disk glass substrate of the present exemplary embodiment is an annular thin glass substrate. The size of the magnetic disk glass substrate is not particularly limited. However, the magnetic disk glass substrate preferably has a nominal diameter of 2.5 inches, for instance.

(Manufacturing Method of Glass Substrate for Magnetic Disk)

A manufacturing method of a magnetic disk glass substrate according to the present exemplary embodiment will be hereinafter explained on a step-by-step basis. It should be noted that the order of steps may be arbitrarily changed.

(1) Molding of Plate Glass and Lapping Step

For example, in a molding step of a plate glass using a float method, molten glass having e.g., the aforementioned composition is firstly poured continuously into a tub filled with molten metal (e.g., tin) in order to obtain a plate glass. The molten glass flows along a travel direction within the strictly temperature-controlled tub, and a plate glass having thickness and width regulated to desired dimension is finally produced. Through the cutting of the plate glass, a plate glass material with a predetermined shape is obtained as a blank of the magnetic disk glass substrate. The plate glass material herein obtained by the float method has a sufficiently flat surface due to the horizontal surface of molten tin filled in the tub.

On the other hand, in a molding step of the plate glass using press-molding, for instance, glass gob made of molten glass is supplied to a bottom mold as a receiver gob forming mold. Subsequently, the glass gob is press-molded using the bottom mold and a top mold as an opposed gob forming mold. More specifically, the glass gob made of molten glass is supplied onto the bottom mold, and subsequently, the bottom face of a top-mold side barrel and the top face of a bottom-mold side barrel are contacted to each other. Accordingly, a thin plate glass molding space is externally produced across a slid surface between the top mold and the top-mold side barrel and a slid surface between the bottom mold and the bottom-mold side barrel. Further, the top mold is lowered for executing press-molding and is elevated immediately after the press-molding. Accordingly, a plate glass material is formed as the blank of the magnetic disk glass substrate.

It should be noted that the method of manufacturing the plate glass material is not limited to the above. For example, the plate glass material can be manufactured using any suitable heretofore known manufacturing methods such as a down-draw method, a re-draw method and a fusion method.

Next, a lapping processing is executed for the both principal faces of the plate glass material cut in a predetermined shape using alumina-system loose abrasive grains on an as-needed basis. Specifically, the lapping processing is executed as follows. First, top and bottom lap platens are pressed onto the both principal faces of the plate glass material. Grinding liquid (slurry) containing loose abrasive grains is herein supplied onto the principal faces of the plate glass material. Under the condition, the top and bottom lap platens are moved relatively to each other. It should be noted that, when the plate glass material is molded by means of a float method, the post-molding principal faces have a highly accurate surface roughness. In this case, the lapping processing may be omitted.

(2) Coring Step

An annular glass substrate is produced by forming an inner hole in the center part of the disc-shaped glass material using a cylindrical diamond drill.

(3) Chamfering Step

A chamfering step is executed for forming chamfered portions on the edges (i.e., inner and outer peripheral edges) after execution of the coring step. In the chamfering step, chamfering is executed for the inner and outer peripheral edges of the annular glass substrate by means of, for instance, a metal bond abrasive block using diamond abrasive grains. Thus, the chamfered portions are formed.

(4) Edge Polishing Step (Machining Step)

Next, edge polishing is executed for the annular glass substrate.

In the edge polishing step, mirror finishing is executed for the inner peripheral edge and the outer peripheral edge of the glass substrate by means of brush polishing. Slurry, containing fine particles of e.g., cerium oxide as loose abrasive grains, is herein used. Contamination (attachment of dirt, etc.) and breakage (damage, flaws, etc.) on the edges of the glass substrate are eliminated by means of edge polishing. It is thereby possible to prevent occurrence of thermal asperity and deposition of ions (sodium ion, potassium ion, etc.) attributed to corrosion.

(5) Grinding Step Using Fixed Abrasive Grains

In a grinding step using fixed abrasive grains, the principal faces of the annular glass substrate are ground by a double-face grinder device including a planetary gear mechanism. For example, the removal stock for grinding is set to be roughly several μm to 100 μm. The double face grinder device includes a pair of platens (i.e., top and bottom platens). The annular glass substrate is interposed and held between the top and bottom platens. Subsequently, the glass substrate and the respective top and bottom platens are moved relatively to each other by operating and moving either or both of the top and bottom platens. Accordingly, the both principal faces of the glass substrate can be ground.

Furthermore, in executing a first polishing step which will be described later, the surface roughness Ra of a principal face of the glass substrate is preferably set to be less than or equal to 0.1 μm. By doing so, the removal stock of the principal face of the glass substrate cannot be excessively increased and the surface roughness can be fully lowered in the first polishing step. Too much removal stock of the principal face of the glass substrate degrades the edge shape in the first polishing step.

(6) First Polishing (Principal Face Polishing) Step

Next, a first polishing step is executed for the ground principal faces of the glass substrate. For example, the removal stock for the first polishing step is set to be roughly several μm to 50 μm. By setting the removal stock in this range, the surface roughness can be fully decreased while the degradation of the edge shape is suppressed. It is an object of the first polishing step to eliminate flaws and distortion left on the principal faces after the grinding step using the fixed abrasive grain and to regulate waviness or micro waviness.

(Polisher Device)

The polisher device to be used in the first polishing step will be hereinafter explained with reference to FIG. 1. FIG. 1 is a schematic cross-sectional view of the polisher device (double-face polisher device) to be used in the first polishing step. It should be noted that the structure of the polisher device may be applied to the grinder device to be used in the aforementioned grinding step.

As illustrated in FIG. 1, the polisher device includes a pair of top and bottom platens (i.e., a top platen 40 and a bottom platen 50). An annular glass substrate G is interposed and held between the top platen 40 and the bottom platen 50. The glass substrate G and the respective top and bottom platens 40 and 50 are moved relatively to each other by operating and moving either or both of the top and bottom platens 40 and 50. Accordingly, the both principal faces of the glass substrate G can be polished.

The structure of the polisher device will be more specifically explained with reference to FIG. 1.

In the polisher device, a pair of polisher pads 10 is attached to the top face of the bottom platen 50 and the bottom face of the top platen 40. Each polisher pad 10 is a plate member formed in an entirely annular shape. A planetary gear mechanism, as a whole, is formed about a center axis CTR by a sun gear 61, an internal gear 62 disposed on an outer edge and a disc-shaped carrier 30. The disc-shaped carrier 30 is meshed at its inner periphery with the sun gear 61, while being meshed at its outer periphery with the internal gear 62. Further, the disc-shaped carrier 30 accommodates and holds a single or plurality of the plate glass substrates G (work/works). On the bottom platen 50, the carrier 30 rotates and revolves as a planetary gear, while the glass substrate/substrates G and the bottom platen 50 are moved relatively to each other. When the sun gear 61 is rotated in a CCW (counter-clockwise) direction, for instance, the carrier 30 is rotated in a CW (clockwise) direction. The internal gear 62 is accordingly rotated in the CCW direction. As a result, relative motion is produced between the bottom-side polisher pad 10 and the glass substrate/substrates G. Likewise, the glass substrate/substrates G and the top platen 40 may be moved relatively to each other.

In the course of the aforementioned relative motion, the top platen 40 is pressed onto the glass substrate/substrates G (i.e., in the vertical direction) with a predetermined load. In other words, the polisher pads 10 are pressed onto the plate glass substrate/substrates G. Further, a pump (not illustrated in the figure) is configured to supply a slurry from a slurry supply tank 71 to spaces between the glass substrate/substrates G and the polisher pads 10 through a single or plurality of pipes 72. The principal faces of the glass substrate/substrates G are polished by means of an abrasive contained in the slurry. The slurry, herein used for polishing the glass substrate/substrates G is preferably discharged from the top and bottom platens and is then returned to the slurry supply tank 71 through a single or plurality of return pipes (not illustrated in the figure) for a reuse purpose.

As material for the polisher pad 10, material impregnated with abrasive grains, for example, urethane foam, can be used optimally. Hardness of the polisher pad 10 is preferably set to be 80 to 100, and is more preferably set to be 90 to 100 in JIS-A hardness. When the hardness of the polisher pad 10 is set to be 80 or more in JIS-A hardness, the good edge shape of the glass substrate in the first polishing step can be obtained. The abrasive grains to be impregnated are cerium oxide, for example. It is preferable to set an average particle size of the abrasive grains to be 1 to 2 μm and the impregnation amount to be 25 to 35% by weight. This is because when the impregnation amount is less than or equal to 25%, brittleness of the polisher pad lacks, so that slurry is easy to cause plugging and the polishing rate is decreased in serial production. When the impregnation amount is greater than or equal to 35%, brittleness of the polisher pad makes it difficult to maintain the initial properties of the polisher pad for a long time.

Here, the average particle size (D50) means a 50% particle size in cumulative volume frequency calculated by volume fraction when measured from the smallest particle size.

It should be noted that in the polisher device, the load of the top platen 40 to be applied to the glass substrate/substrates G is preferably regulated for setting a desired polishing load to be applied to the glass substrate/substrates G. From the perspective of achieving a high polishing speed, the polishing load is preferably greater than or equal to 50 g/cm$^2$, further preferably greater than or equal to 70 g/cm$^2$, and yet further preferably greater than or equal to 90 g/cm$^2$. Further, from the perspective of reducing scratches and stabilizing quality, the polishing load is preferably less than or equal to 180 g/cm$^2$, further preferably less than or equal to 160 g/cm$^2$, and yet further preferably less than or equal to 140 g/cm$^2$. Put the above together, the polishing load is preferably in a range of 50 to 180 g/cm$^2$, further preferably in a range of 70 to 160 g/cm$^2$, and yet further preferably in a range of 90 to 140 g/cm$^2$.

The supply speed of the slurry in polishing processing depends on the polisher pads 10, the composition and density of the slurry and the size of the glass substrate/substrates G. However, from the perspective of enhancing the polishing speed, the supply speed is preferably in a range of 500 to 5000 ml/min, further preferably in a range of 1000 to 4500 ml/min, and yet further preferably in a range of 1500 to 4000 ml/min. The rotational speed of the polisher pads 10 is preferably in a range of 10 to 50 rpm, further preferably in a range of 20 to 40 rpm and yet further preferably in a range of 25 to 35 rpm.

The slurry to be used in the polisher device of FIG. 1 contains zirconium oxide abrasive grains having monoclinic crystalline structures (hereinafter may be simply referred to as "monoclinic structures") and tetragonal crystalline structures (hereinafter may be simply referred to as "tetragonal structures") as an abrasive. The zirconium oxide abrasive grains in the present exemplary embodiment may not contain stabilizing agent such as yttrium, yttrium oxide, or the like.

The slurry can be prepared as follows. First, monoclinic zirconium oxide of the room temperature is sintered for an appropriate period of time while being kept at a temperature of for instance, roughly 1,000 to 1,200 degrees Celsius about 1,000 degrees Celsius, which is closer to the temperature that phase transmission of zirconium oxide begins from the monoclinic structure to the tetragonal structure. Accordingly, coarse powder is obtained. Subsequently, an appropriate amount of water, and further arbitrarily, additives (e.g., a dispersant, a re-aggregation inhibitor, a pH adjustor, an electric charge modifier, a polymer flocculant, etc.) are added to the zirconium oxide powder with a desired average particle size (diameter) obtained from the coarse powder. The slurry is thus prepared.

As the dispersant, phosphate, sulfonate, polycarboxylic acid, polycarboxylate or etc. can be herein used. As phosphate amongst the above, sodium hexametaphosphate, sodium pyrophosphate, potassium pyrophosphate or etc. can be preferably used. As the re-aggregation inhibitor, fiber or sugar (e.g., cellulose, carboxymethyl cellulose, maltose, fructose, etc.) can be preferably used. From the perspective of dispersibility of the abrasive, pH is preferably set to be greater than or equal to 6.0 and less than or equal to 12.0.

The average particle size is preferably set to be greater than or equal to 0.1 μm and less than or equal to 5 μm, and is more preferably set to be greater than or equal to 0.2 μm and less than or equal to 0.5 μm. Moreover, it is further preferable to set the standard deviation SD of the particle size to be greater than or equal to 0.05 μm and less than or equal to 0.15 μm. Accordingly, the good surface roughness of the principal face of the glass substrate and the good edge shape of the glass substrate can be obtained while the degree of the polishing rate and the existence of nano scratches are well maintained.

The amount of zirconium oxide abrasive grains contained in the slurry is preferably set to be in a range of 1 to 25% by weight. By setting the amount in this range, the high level of both the surface roughness of the principal face of the glass substrate and the polishing rate of the glass substrate can be achieved.

When sintered under the aforementioned conditions, zirconium oxide abrasive grains can be formed as those having both of the monoclinic crystalline structures and the tetragonal crystalline structures. As a result, the abrasive grains acquire a roughly mid-hardness between the hardness of the monoclinic abrasive grains and that of the tetragonal abrasive grains. The mid-hardness is appropriate for polishing the principal faces of the glass substrate.

Variation in a particle size distribution between before and after the polishing processing using zirconium oxide abrasive grains fabricated at different sintering temperatures will be hereinafter explained regarding a sintering temperature of less than 900 degrees Celsius (low temperature), a sintering temperature of 1,000 degrees Celsius (middle temperature) and a sintering temperature of 1,100 degrees Celsius (high temperature).

When the sintering temperature is lower than 900 degrees Celsius, the herein fabricated zirconium oxide abrasive grains are formed only by the monoclinic structures, and therefore, have a low hardness. When the principal faces of the glass substrate is polished using the zirconium oxide abrasive grains as an abrasive, fracturing of the abrasive grains is caused during polishing. Therefore, the particle size distribution is shifted towards a low particle size due to the fracturing of the abrasive grains and a ratio of the abrasive grains with a relatively large particle size is reduced. As a result, polishing is executed while a load locally acts on the abrasive grains with a large particle size. Therefore, nano scratches and/or nano pits tend to be produced on the principal faces of the glass substrate.

When the sintering temperature is 1,000 degrees Celsius, the herein fabricated zirconium oxide abrasive grains are also formed only by the monoclinic structures. However, the hardness thereof is increased by the amount of increase in sintering temperature. As a result, shifting of the particle size distribution towards a low particle size, which is attributed to the fracturing of the abrasive grains by polishing, is inhibited. In this case, however, polishing is executed while a load locally acts on the abrasive grains with a large particle size. Therefore, nano scratches and/or nano pits tend to be produced on the principal faces of the glass substrate.

When the sintering temperature is 1,100 degrees Celsius, the herein fabricated zirconium oxide abrasive grains simultaneously contain crystallites of the monoclinic crystalline structure and those of the tetragonal crystalline structure under a condition of room temperature. When crystallites of the monoclinic crystalline structure and those of the tetragonal crystalline structure are mixed, the zirconium oxide abrasive grains have a hardness greater than that of the zirconium oxide abrasive grains containing only crystallites of the monoclinic crystalline structure. Fracturing of the abrasive grains is thereby less easily caused during polishing when the principal faces of the glass substrate are polished using the zirconium oxide abrasive grains as an abrasive. Therefore, the particle size distribution less varies between before and after the polishing processing and polishing can be stably executed. In this case, due to less variation in the particle size distribution, chances are low that a load locally acts on the abrasive grains, and therefore, nano scratches and/or nano pits are less easily produced on the principal faces of the glass substrate.

Further, the zirconium oxide abrasive grains, simultaneously containing crystallites of the monoclinic crystalline structure and those of the tetragonal crystalline structure, have a hardness less than that of stabilized (or partially stabilized) zirconia abrasive grains containing crystallites of the tetragonal crystalline structure. Therefore, nano scratches and/or nano pits are less easily produced on the principal faces of the glass substrate during polishing. For example, the depth of nano scratches and/or nano pits can be set to be less than or equal to 250 nm.

Figure 2:
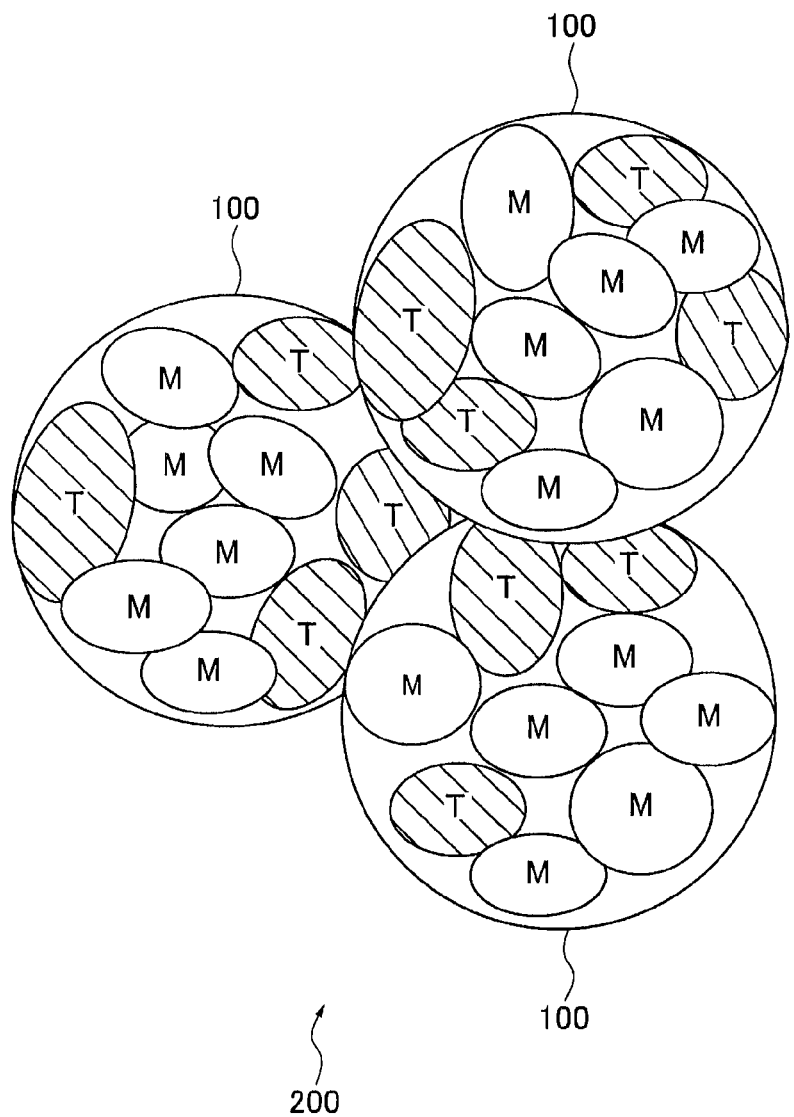
FIG. 2 is a schematic diagram of the polycrystalline structure of a zirconium oxide abrasive grain.

FIG. 2 is a schematic diagram illustrating the structure of the zirconium oxide abrasive grains when the sintering temperature is 1,100 degrees Celsius. The diameter of a single primary particle of zirconium oxide is preferably greater than or equal to 30 nm and less than or equal to 2 μm, more preferably less than or equal to 200 nm. As described above, the average particle size is preferably greater than or equal to 0.1 μm and less than or equal to 5 μm in an aggregate (which is a base unit as an abrasive grain and may be referred to as "a secondary particle") formed by a plurality of primary particles sintered by means of sintering. FIG. 2 exemplifies an aggregate 200 formed by three primary particles 100.

As illustrated in FIG. 2, when the sintering temperature is 1,100 degrees Celsius, each primary particle of zirconium oxide simultaneously contains crystallites of the monoclinic crystalline structure indicated with "M" and those of the tetragonal crystalline structure indicated with "T", while the primary particles are sintered (aggregated) to each other. When the sintering temperature is changed about 1,100 degrees Celsius, a ratio between the amounts of the monoclinic and tetragonal crystalline structures contained in zirconium oxide particles varies, and the hardness of zirconium oxide particles also varies in accordance with the ingredient amount of the crystallites of the tetragonal crystalline structure having a higher hardness. When the sintering temperature remarkably exceeds 1,100 degrees Celsius, phase transition to crystallites of the tetragonal crystalline structure is caused in the zirconium oxide abrasive grains. However, when it is returned to the room temperature, phase transition to crystallites of the monoclinic crystalline structure is caused therein. On the other hand, a ratio between the amounts of the monoclinic and tetragonal crystalline structures contained in the zirconium oxide particles is correlated to sintering conditions (e.g., a temperature) when the zirconium oxide abrasive grains are fabricated at a predetermined temperature range about 1,100 degrees Celsius (e.g., a sintering temperature of 1,000 to 1,200 degrees Celsius) that phase transition begins from the monoclinic crystalline structure to the tetragonal crystalline structure in zirconium oxide. Therefore, the sintering temperature, for instance, can be determined so that an appropriate hardness can be achieved depending on a glass substrate as a polishing target. A ratio of the amount of the tetragonal crystalline structures is preferably roughly several % although it depends on a sintering condition.

The size of the crystallites is preferably in a range of roughly 20 to 60 nm. For example, the size may be 40 nm.

The reason why the diameter of a single primary particle of zirconium oxide is preferably greater than or equal to 30 nm and less than or equal to 2 μm, is considered as follows. The number of contact points with a principal face of the substrate is more increased during the polishing processing as the diameter of a primary particle of zirconium oxide becomes smaller (in other words, a increased number of primary particles contact the principal face of the substrate), so that each primary particle receives less force from the platen relatively, and therefore scratches produced on the glass substrate are reduced. On the other hand, when a primary particle of zirconium abrasive grains is too small, the contact area of the primary particle and the glass substrate is reduced, which makes the zirconium abrasive grains easy to slip on the glass substrate during the polishing processing. Consequently, the polishing function cannot be effective, and polishing rate is decreased.

It should be noted that the reason is not clear that the tetragonal crystalline structures are left in the zirconium oxide particles even though sintering is executed in a predetermined temperature range about 1,100 degrees Celsius and it is then returned to room temperature. However, the reason can be assumed as follows. In short, multiple crystallites, forming the zirconium oxide particles, are only partially phase-transited to the tetragonal crystalline structures by executing sintering at a temperature closer to the lower limit temperature that phase transition to the tetragonal crystalline structures is caused. The phase-transited crystallites are herein supposed to be roughly entirely enclosed by crystallites of the monoclinic crystalline structures. As a result, the crystallites of the tetragonal crystalline structures are thus isolated and thereby stabilized. Therefore, the crystallites of the tetragonal crystalline structures are not returned to the monoclinic crystalline structures even when it is returned to room temperature. On the other hand, when the crystallites of the monoclinic crystalline structures are phase-transited to the tetragonal structures together with the crystallites in the surrounding thereof, it can be assumed that those crystallites are phase-transited all at once because they are liable to be affected by the surrounding thereof when it is returned to room temperature.

A ratio between the amounts of the monoclinic and tetragonal crystalline structures contained in the zirconium oxide particles can be measured using an x-ray powder diffraction device. The x-ray powder diffraction device utilizes the fact that diffraction angles, formed in irradiating x-ray to a sample of zirconium oxide particles made of polycrystal, vary in accordance with the types of the crystalline structures. In general, a measurement result is represented where the horizontal axis indicates 2θ while the vertical axis indicates diffraction intensity (Intensity). Namely, in the measurement result, a value of 2θ where a peak intensity can be obtained and a value of the peak intensity are different between the monoclinic crystalline structures and the tetragonal crystalline structures because of difference in crystalline structures.

The peak intensity of the monoclinic crystalline structure can be set as a peak area (integrated intensity) corresponding to a crystal face "hkl=−111", while the peak intensity of the tetragonal crystalline structure can be set as a peak area corresponding to a crystal face "hkl=101". A peak position can be obtained by the Bragg's formula "2d Sin θ=nλ". In the Bragg's formula, d is a distance between crystal faces; θ is a diffraction angle (an angle formed by a crystal face and x-ray); λ is a wavelength of x-ray; and n is a whole number. As to abrasive grains with crystal faces that are randomly aligned but could be aligned in orientations, it is required to execute measurement using the x-ray powder diffraction method under a condition without impact of orientation.

When the x-ray powder diffraction device is used, a ratio between the amounts of the monoclinic and tetragonal crystalline structures can be calculated by a ratio of the peak intensity of the tetragonal crystalline structures (e.g., the peak position: 2θ=30.1) with respect to the peak intensity of the monoclinic crystalline structures (e.g., the peak position: 2θ=28.1).

Polishing is executed in the first polishing step with the following settings for the surface asperity of the principal faces of the glass substrate. That is, a roughness (Ra) is set to be less than or equal to 0.5 nm, while a micro-waviness (MW-Rq) is set to be less than or equal to 0.5 nm. Furthermore, the roughness (Ra) is more preferably set to be less than or equal to 0.4 nm, because removal stock in a last polishing step which is the subsequent step, is reduced and the edge shape can be avoided to degrade.

The micro-waviness can be herein expressed by a value of RMS (Rq) to be calculated as a roughness at a wavelength band of 100 to 500 μm in a range having a radius of 14.0 to 31.5 mm on the entire principal face. For example, the micro-waviness can be measured by a Model-4224 of Polytech corporation.

The roughness of the principal face can be expressed by an arithmetic average roughness Ra defined based on JIS B0601: 2001. When being greater than or equal to 0.006 μm and less than or equal to 200 μm, the arithmetic average roughness Ra can be measured by, for instance, Surliest SV-3100 series of Mitsutoyo Co., Ltd. and can be calculated by a method defined based on JIS B0633:2001. As a result, when being less than or equal to 0.03 μm, the arithmetic average roughness Ra can be measured by, for instance, Nanoscope scanning probe microscope (Atomic Force Microscope: AFM) of Japan Veeco Co., Ltd. and can be calculated by a method defined based on JIS R1683:2007. In the present application, it is possible to use the arithmetic average roughness Ra measured with a resolution of 512×512 pixels in a square measurement area of 1 μm×1 μm.

In the first polishing step, a Dub-off value showing the edge shape of the principal face of the glass substrate are preferably set to be 0 to +10 nm, and more preferably set to be 0 to +5 nm. A Dub-off value, the calculation method of which will be described later, is a value to be the basis of evaluation criteria of the edges shape. The edge shape of the glass substrate is recognized to be better as the absolute value of a Dub-off value becomes smaller. When a Dub-off value is set to be in the range as above in the polishing step, the Dub-off value is easy to finally fall in a range of +2 to +10 nm by a final polishing step (a polishing step using a minute colloidal silica for finally making the surface roughness extremely small), which will be described later. It should be noted that the polishing using a minute colloidal silica tends to direct a Dub-off value to the plus side. The reason why setting the final dub-off value to be in the range as above (a slight roll-off shape; see FIG. 3A) is that floating of a head at the outermost periphery portion of the principal face, where flattering requirement is the severest, is stabilized so that an element portion of a DFH mechanism can be largely protruded.

(7) Chemical Strengthening Step

Next, the glass substrate is chemically strengthened after the first polishing step.

For example, a mixed liquid of (60% by weight of) potassium nitrate and (40% by weight of) sodium sulfate may be used as a chemical strengthening liquid. In the chemical strengthening, a chemical strengthening liquid is heated to e.g., 300 to 400 degrees Celsius, and a washed glass substrate preliminarily heated to e.g., 200 to 300 degrees Celsius is submerged into the chemical strengthening liquid for e.g., 1 to 5 hours. To chemically strengthen the entire principal faces of Multiple substrates, the submerging is preferably executed under the condition that the glass substrates are accommodated in holders while being held at the edges thereof.

In thus submerging the glass substrate into the chemical strengthening liquid, lithium ions and sodium ions on the outermost layer of the glass substrate are respectively substituted into sodium ions and potassium ions respectively having a relatively large ionic radius within the chemical strengthening liquid. Accordingly, the glass substrate is strengthened. It should be noted that the chemically strengthened glass substrate is washed. For example, the chemically strengthened glass substrate is washed by sulfuric acid and is then washed by pure water or the like.

(8) Second (Final) Polishing Step (Post Polishing Step)

Next, a second polishing step is executed for the glass substrate chemically strengthened and sufficiently washed. The second polishing step is intended to mirror-polish the principal faces of the glass substrate. In the second polishing step, the removal stock is set to be less than or equal to 5 μnm. The removal stock is preferably set to be greater than or equal to ten times as much as the depth of nano pits and/or nano scratches to be produced in the first polishing step in order to stably mass-produce substrates that all the nano pits and/or nano scratches are removed in the second polishing step. In the present exemplary embodiment, the depth of nano pits and/or nano scratches to be produced in the first polishing step can be set to be less than or equal to 250 nm. Therefore, the removal stock (i.e., a combined value of the removal stocks of the top and bottom faces) can be set to be less than or equal to 5 μm in the second polishing step.

For example, the polisher device used in the first polishing step is used in the second polishing step. The second polishing step is different from the first polishing step in the type and the particle size of loose abrasive grains and hardness of a resin polisher.

The abrasive grains other than zirconium oxide abrasive grains, for example, fine particles (particle size: a diameter of roughly 10 to 50 nm) of colloidal silica mixed into the slurry, are used as the loose abrasive grains to be used in the second polishing step. Accordingly, the surface roughness of the principal face of the glass substrate can be further decreased to adjust the edge shape in a preferable range. Furthermore, according to a study by the inventors, zirconium oxide abrasive grains are found to be easy to adhere to the surface of the polished glass substrate. However, by using abrasive grains other than the zirconium oxide abrasive grains in the final polishing, the zirconium oxide abrasive grains adhered to the principal face or the side wall surface can be removed physically.

The polished glass substrate is washed by neutral detergent, pure water, IPA or etc. Accordingly, a magnetic disk glass substrate is obtained.

(Magnetic Disk)

The magnetic disk is obtained using a magnetic disk glass substrate as follows.

For example, the magnetic disk has a structure that multiple layers, at least including an adhesive layer, an underlying layer, a magnetic layer (magnetic recording layer), a protective layer and a wetting layer, are sequentially laminated in this order from bottom to top on a principal face of a magnetic disk glass substrate (hereinafter simply referred to as "a substrate").

For example, the substrate is introduced into a vacuumed film forming device, and the adhesive layer, the underlying layer and the magnetic layer are sequentially formed atop the principal face of the substrate in an Ar atmosphere by means of DC magnetron sputtering. For example, CrTi may be used as the adhesive layer, while CrRu may be used as the underlying layer. For example, CoPt alloy may be used as the magnetic layer. Alternatively, CoPt alloy or FePt alloy, having the L10 ordered structure, may be formed as the magnetic layer for heat assisted magnetic recording. After the formation of the layers, the protective layer is formed, for instance, using $C_2H_4$ by means of a CVD method. Next, a nitriding treatment is executed by introducing nitrogen into the surface. Accordingly, the magnetic recording medium can be formed. Subsequently, the wetting layer can be formed by applying e.g., PFPE (perfluoropolyether) onto the protective layer by means of a dip coating method.

The fabricated magnetic disk, together with a magnetic head embedded with a DFH (Dynamic Flying Height) Control mechanism, is preferably installed in a HDD (Hard Disk Drive) as a magnetic recording/reproducing device.

<Second Exemplary Embodiment>

A manufacturing method of a glass substrate for a magnetic disk according to a second exemplary embodiment will be hereinafter explained. A magnetic disk glass substrate to be manufactured by the manufacturing method of the present exemplary embodiment is the same as that manufactured in the first exemplary embodiment. Further, the manufacturing method of the present exemplary embodiment is different from that of the first exemplary embodiment regarding the abrasive contained in the slurry to be used in the first polishing (principal face polishing) step.

It should be noted that a fracture toughness value $K_{1c}$ of the glass substrate is preferably set to be 0.4 to 1.5 [MPa·m$^{1/2}$], and more preferably set to be 0.5 to 1.0 in Vickers hardness testing in the present exemplary embodiment.

In the present exemplary embodiment, the slurry to be used for the polisher device of FIG. 1 contains, as the abrasive, abrasive grains of partially stabilized zirconia (hereinafter referred to as "yttrium-contained zirconia") that contains either yttrium or yttrium oxide as a stabilizing agent. The shiny can be prepared as follows. First, an appropriate amount of water, and further arbitrarily, additives (e.g., a dispersant, a re-aggregation inhibitor, a pH adjustor, an electric charge modifier, a polymer flocculant, etc.) are added to the yttrium-contained zirconia powder with a desired average particle size obtained from the coarse powder of yttrium-contained zirconia. The slurry is thus prepared.

As the dispersant, phosphate, sulfonate, polycarboxylic acid, polycarboxylate or etc. can be herein used. As phosphate amongst the above, sodium hexametaphosphate, sodium pyrophosphate, potassium pyrophosphate or etc. can be preferably used. From the perspective of enhancement in dispersion stability, the amount of the dispersant contained in the slurry is preferably in a range of 0.01 to 3.0% by weight, further preferably in a range of 0.1 to 2.0% by weight, and yet further preferably in a range of 0.5 to 1.0% by weight, with respect to the weight of the adhesive. As the re-aggregation inhibitor, fiber of sugar (e.g., cellulose, carboxymethyl cellulose, maltose, fructose, etc.) can be preferably used. From the perspective of dispersibility of the abrasive, pH is preferably set to be greater than or equal to 6.0 and less than or equal to 12.0.

The mole ratio of yttrium oxide (yttria) contained in the abrasive (yttrium-contained zirconia) is preferably set to be in a range of 1 to 6%, and more preferably set to be in a range of 2 to 5%. When the mole ratio of the yttria is too small, nano pits or nano scratches are easy to be produced on the principal face of the polished glass substrate and the edge shape is degraded. When the mole ratio of the yttria is too large, flaws are readily caused on the principal face of the polished glass substrate.

From the perspective of enhancement in the polishing speed, the amount of yttrium-contained zirconia abrasive grains contained in the slurry is preferably greater than or equal to 1% by weight, further preferably greater than or equal to 5% by weight, and yet further preferably greater than or equal to 10% by weight. Further, from the perspective of dispersibility and cost reduction, the amount of yttrium-contained zirconia abrasive grains contained in the slurry is preferably less than or equal to 30% by weight, further preferably less than or equal to 20% by weight, and yet further preferably less than or equal to 15% by weight. In other words, the amount of yttrium-contained zirconia abrasive grains contained in the slurry is preferably in a range of 1 to 30% by weight, further preferably in a range of 5 to 20% by weight, and yet further preferably in a range of 10 to 15% by weight.

It should be noted that the aforementioned contained amount refers to a contained amount in preparing the slurry. The slurry may be preserved in a concentrated state and may be diluted in use for obtaining the aforementioned contained amount.

From the perspective of enhancement in the polishing speed, the average particle size (D50) of yttrium-contained zirconia abrasive grains is preferably in a range of 0.10 to 0.60 µm and further preferably in a range of 0.20 to 0.40 µm. The average particle size (D50) herein refers to a particle size that a cumulative volume frequency thereof, calculated by volume fraction, is 50% when calculated from the smaller particle size side. Further, similarly from the perspective of enhancement in the polishing speed by effectively utilizing the entirety of the abrasive grains, the particle sizes of the abrasive grains are preferably equalized and standard deviation (SD) of yttrium-contained zirconia abrasive grains in the slurry is preferably less than or equal to 1 µm, further preferably less than or equal to 0.5 µm, and yet further preferably less than or equal to 0.2 µm.

The cubic crystalline structures are preferably contained most in the zirconia crystalline structures contained in yttrium-contained zirconia abrasive grains to be used as the abrasive. Cubic zirconia, containing the cubic crystalline structures most, has a high hardness (Mohs hardness of 8 to 8.5). Therefore, fracturing of abrasive grains is less easily caused during polishing, compared to zirconia mainly containing the tetragonal crystalline structures (tetragonal zirconia). As a result, compared to the tetragonal zirconia, an advantageous effect can be further achieved that the particle size distribution less easily varies and scratches are less easily produced on the principal faces of the glass substrate.

The major component of the zirconia's crystalline structures contained in yttrium-contained zirconia abrasive grains can be determined by the x-ray powder diffraction device. The x-ray powder diffraction device utilizes the fact that diffraction angles, formed in irradiating x-ray (CuKα1 ray, λ=0.154 nm) to a sample of yttrium-contained zirconia particles containing zirconium oxide made of polycrystal, vary in accordance with the types of the crystalline structures of zirconia. In general, a measurement result is represented where the horizontal axis indicates 2θ (θ: Bragg's angle) while the vertical axis indicates diffraction intensity (Intensity). In the measurement result by the x-ray powder diffraction device, a value of 2θ where a peak intensity can be obtained and a value of the peak intensity vary in accordance with the types of the crystalline structures. For example, it has been known that values of 2θ are 28.1750 [deg], 31.4680 [deg] and 34.3830 [deg], where the peak intensity of the monoclinic crystalline structures can be obtained; a value of 2θ is 29.812 [deg], where the peak intensity of the tetragonal crystalline structures can be obtained; and a value of 2θ is 30.1200 [deg], where the peak intensity of the cubic crystalline structures can be obtained. It should be noted that the aforementioned values of 2θ indicate peak positions that x-ray is most strongly diffracted in the respective crystalline structures. Therefore, it is possible to determine which type of the crystalline structures is the major component by observing peak values of diffraction intensity with respect to values of 2θ varying in accordance with the types of the crystalline structures in the measurement result by the x-ray powder diffraction device and further observing which of the peak values corresponding to the crystalline structures is the maximum value.

Material impregnated with abrasive grains, for example urethane foam, can be optimally used for the polisher pad 10 in the present exemplary embodiment as same as in the first exemplary embodiment. Hardness of the polisher pad 10 is preferably set to be 80 to 100, and more preferably set to be 90 to 100 in JIS-A hardness. By setting the hardness of the polisher pad 10 to be greater than or equal to 80 in JIS-A hardness, the good edge shape of the glass substrate in the first polishing step can be obtained. The abrasive grains to be impregnated are cerium oxide, for example. The average particle size is preferably set to be 1 to 2 μm, and the impregnation amount is preferably set to be 25 to 35% by weight. When the impregnation amount is less than or equal to 25%, brittleness of the polisher pad lacks, so that slurry is easy to cause plugging and the polishing rate is decreased in serial production. When the impregnation amount is greater than or equal to 35%, brittleness of the polisher pad makes it difficult to maintain the initial properties of the polisher pad for a long time.

(Practical Examples)

The present invention will be hereinafter further explained by practical examples. It should be noted that the present invention is not limited to embodiments described in the practical examples.

(1) Fabrication of Molten Glass

Mixture material was prepared by weighing and mixing materials for obtaining a glass with the following composition. The mixture material was put into a melting container and was therein heated, melted, clarified and stirred. Thus, a uniform molten glass without bubbles and unmelted substances was fabricated. It was confirmed that the obtained glass did not include bubbles and unmelted substances, deposition of crystals, contaminant of refractory substances and/or platinum forming the melting container.

(Glass Composition)

The prepared glass was aluminosilicate glass having the following oxide-based converted composition of: 50 to 75% by mole of $SiO_2$; 1 to 15% by mole of $Al_2O_3$; totally 5 to 35% by mole of at least one selected from the group of $Li_2O$, $Na_2O$ and $K_2O$; totally 0 to 20% by mole of at least one selected from the group of MgO, CaO, SrO, BaO and ZnO; and totally 0 to 10% by mole of at least one selected from the group of $ZrO_2$, $TiO_2$, $La_2O_3$, $Y_2O_3$, $Ta_2O_5$, $Nb_2O_5$ and $HfO_2$, and having the fracture toughness value of 0.7 [$MPa \cdot m^{1/2}$]. Specifically, the glass was prepared to have a composition containing 64.1% by weight of $SiO_2$, 14.7% by weight of $Al_2O_3$, 3.6% by weight of $Li_2O$, 11.1% by weight of $Na_2O$, 0.4% by weight of $K_2O$, 0.6% by weight of MgO, 2.0% by weight of $ZrO_2$, and 1.6% by weight of CaO. 1.9% by weight of $Nb_2O_5$ was also contained as clarifying agent.

(2) Fabrication of Glass Substrate

The aforementioned molten glass, clarified and homogenized, was poured from the pipe(s) onto a bottom mold for press-molding at a predetermined flow rate. The poured molten glass was then cut by a cutting blade for obtaining a predetermined amount of molten glass gob onto the bottom mold. The bottom mold with the molten glass gob disposed thereon was immediately transported from the position below the pipe(s) to a predetermined position. The molten glass gob disposed on the bottom mold was press-molded in a thin disc shape using a top mold opposed to the bottom mold and a barrel. The press-molded product was cooled down to a temperature not causing deformation of the press-molded product. The cooled press-molded product was removed out of the molds, and was then annealed to obtain a glass blank of amorphous. Subsequently, a lapping processing was executed for the glass blank obtained by the press-molding. In the lapping processing, alumina abrasive grains (a particle size of #1000) were used as loose abrasive grains.

(3) Coring and Chamfering

An inner hole was formed in the center part of the disc-shaped glass material using a cylindrical diamond drill for obtaining an annular glass substrate (i.e., coring). Then, the inner and outer peripheral edges of the annular glass substrate were ground by means of a diamond abrasive block for executing a predetermined chamfering processing (i.e., chamfering).

(4) Edge polishing Step

Next, mirror polishing was executed for the edges of the annular glass substrate by means of a brush polishing method. Slurry (loose abrasive grains), containing cerium oxide abrasive grains, was herein used as the polishing abrasive grains. Through the edge polishing step, the edges of the glass substrate were processed in a mirror surface state for preventing the raising of dust such as particles.

Through the aforementioned processing, the annular glass substrate with an outer diameter of 65 mm, an inner diameter of 20 mm and a thickness of 0.8 mm was obtained as a polishing target.

(5) First Polishing Step for Principal Face

The glass substrate was set in the polisher device illustrated in FIG. 1 and was polished using the following abrasive liquid containing abrasives of comparative examples and practical examples represented in Tables 1 and 2, and polishing performances were evaluated.

(5-1) Comparative Examples and Practical Examples Represented in Table 1

The slurry used in the polishing step was produced by mixing zirconium oxide abrasive grains (of 10% by weight) of the comparative examples and the practical examples into pure water and sufficiently stirring the mixture. The average particle size of zirconium oxide was herein set to be 1.0 μm. Further, the removal stock was set to be 50 μm. It should be noted that the zirconium oxide abrasive grains of the practical examples were obtained by firstly sintering the monoclinic zirconium oxide of room temperature at sintering temperatures represented in Table 1 for obtaining coarse powder, and then, by fabricating zirconium oxide powder with the aforementioned average particle size from the obtained coarse powder.

It should be noted that in a comparative example 2 of Table 1, stabilized zirconia abrasive grains were used as zirconium oxide abrasive grains and were fabricated by solid-soluting calcium oxide as a stabilizing agent. In stabilized zirconia, the tetragonal crystalline structures are the major component as the structures of crystallites.

The following polisher pad was used in the first polishing step.
Material: urethane foam
JIS-A hardness: 95
Impregnated abrasive grain: cerium oxide
Average particle size of impregnated abrasive grain: 1 to 2 µm
Impregnation amount: 30% by weight It should be noted that in Table 1, "Ratio of Tetragonal Crystalline Structures to Monoclinic Crystalline Structures" refers to a ratio between the amounts of the monoclinic and tetragonal crystalline structures contained in zirconium oxide particles (i.e., (tetragonal crystalline structures)/(monoclinic crystalline structure)). The ratio of crystalline structures was measured by an x-ray diffraction device (manufactured by Mac Science Corp., model: MXP18A_II; x-ray: CuKα, λ=1.5405 Å; sampling interval: 0.0100 deg; scanning speed: 4.0 deg/min; tube voltage: 50 kv; and tube current: 300 mA). A ratio of the peak intensity (peak position: 2θ=30.1) of the tetragonal crystalline structures with respect to the peak intensity (peak position: 2θ=28.1) of the monoclinic crystalline structures was calculated and the calculated ratio was used as the ratio of crystalline structures. The peak intensity herein refers to integrated intensity (area) under the peak corresponding to the respective crystalline structures. Note that the peak position was based on the data of ICDD (International Centre for Diffraction Data).

Regarding existence/non-existence of nano pits and/or nano scratches, evaluations of "Pass" were further categorized into the following evaluation segments in accordance with the depth of nano pits and/or nano scratches.

Excellent . . . Non-existence of nano pits and/or nano scratches having a depth of 200 nm or greater Good . . . Existence of nano pits and/or nano scratches having a depth of 200 nm or greater An observation method of nano pits and/or nano scratches is as follows.

The polished glass substrate was washed and deficient on the principal faces of the polished glass substrate was detected using an OSA (Optical Surface Analyzer). A bright spot, herein detected, was observed by a SEM (Scanning Electron Microscope), and it was determined whether the bright spot was of a convex deficient (attachment of foreign substance) or of a concave deficient (nano pit or nano scratch). When the bright spot was determined as a nano pit or a nano scratch, the depths thereof was measured by the AFM. It should be noted that single spot-shaped concave deficit was defined as a pit whereas either line-shaped concave deficit or a group of pits continuously aligned on the same trajectory was defined as a scratch.

It should be noted that, strictly speaking, the nano pits and/or nano scratches in Table 1 are different from those of a final product. Nano pits and/or nano scratches, which could be problematic in the final product, refer to those with a quite shallow depth of 50 nm or less (in some cases, 10 nm or less). This is because the depth of nano pits and/or nano scratches is shallowed by the second polishing step.

In Table 1, zirconium oxide abrasive grains of the comparative example 1 are formed only by the monoclinic crystalline structures, and therefore, the hardness thereof is low. Due to this, the polishing rate did not satisfy the criteria. Further, as to zirconium oxide abrasive grains of the comparative example 1, the number of abrasive grains with small

TABLE 1

| Zirconium Oxide Abrasive Grains | Sintering Temperature | Ratio of Tetragonal Crystalline Structures to Monoclinic Crystalline Structures | Polishing Rate | Existence/Non-existence of Nano Pits and/or Nano Scratches |
|---|---|---|---|---|
| Comparative Example 1 | Lower than 900 degrees Celsius | 0% | Fail | Fail |
| Practical Example 1 | 1,000 degrees Celsius | 0.70% | Pass | Pass (Good) |
| Practical Example 2 | 1,100 Degrees Celsius | 1.82% | Pass | Pass (Excellent) |
| Practical Example 3 | 1,150 degrees Celsius | 2.16% | Pass | Pass (Excellent) |
| Comparative Example 2 (Stabilized Zirconia) | — | (Only Tetragonal Crystalline structures) | Pass | Fail |

In the evaluation of polishing performances represented in Table 1, "Pass" was given where the following criteria were satisfied, whereas "Fail" was given where the following criteria were not satisfied.
Polishing rate: 1.0 µm/min or greater
Existence/non-existence of nano pits and/or nano scratches: non-existence of nano pits and/or nano scratches having a depth of 250 nm or greater on a principal face after polishing.

particle sizes was increased by fracturing during polishing, and accordingly, deep nano scratches were produced on the principal faces of the glass substrate. As to stabilized zirconia abrasive grains of the comparative example 2, the hardness thereof was too high, and therefore, nano pits and nano scratches were produced on the principal faces of the glass substrate although the polishing rate thereof was good.

On the other hand, zirconium oxide abrasive grains of the practical examples 1 to 3 simultaneously contain the monoclinic crystalline structures and the tetragonal crystalline structures. Obtained were thereby abrasive grains with hardness suitable for the polishing of the principal faces of the glass substrate. As a result, the polishing rate was good, while deep nano pits and/or deep nano scratches were not found on the principal faces of the glass substrate.

It should be noted that in the cases of the practical examples 1 to 3, it was found that the removal stock was less than or equal to 5 μm in the second polishing step, and the surface asperity, the surface roughness, and the edge shape of the principal faces of the glass substrate were also good.

Furthermore, two types of powders of zirconium oxide (average particle size: 1.0 μm) having 2.98% and 3.71% respectively in ratio of the tetragonal crystalline structure relative to the monoclinic crystalline structure, were fabricated by adjusting the sintering time at the sintering temperature (1150 degrees Celsius) as in the practical example 3. The two types of powders were used to polish the principal faces of the glass substrate as in the practical examples 1 to 3 for evaluation (referred to as Practical examples 4 and 5, respectively). As a result, the polishing rate in both of the practical examples 4 and 5 satisfied the criteria. In evaluation of existence of nano pits and nano scratches, the practical example 4 was "Excellent" (in a case where the ratio was 2.98%), and the practical example was "Good" (in a case where the ratio was 3.71%).

Consequently, the evaluation result was good particularly when the ratio of the tetragonal crystalline structure relative to the monoclinic crystalline structure was in a range of 0.7 to 3.0%.

Powders of zirconium oxide were fabricated under the condition that the sintering temperature was the same as in the practical example 2, the ratio of the tetragonal crystalline structure relative to the monoclinic crystalline structure was also the same as in the practical example 2, and the average particle size of the abrasive grains differs from the practical example 2. The average particle size D50 of the powder was 0.3 μm, and the standard deviation SD was 0.1 μm. The powder was used as an abrasive to polish the principal face of the glass substrate for evaluation (referred to as Practical example 6). The amount of nano scratches in the practical example 6 was almost the same as in the practical example 2. The polishing rate was further improved compared to the practical example 2. Moreover, an arithmetic average roughness Ra and Dub-off value of the principal face in the practical example 6 were much better than the practical example 2. Specifically, with respect to the practical example 2, an arithmetic average roughness Ra was 0.5 nm and Dub-off value was +8 nm. With respect to the practical example 6, an arithmetic average roughness Ra was 0.4 nm and Dub-off value is +4 nm.

Furthermore, the principal face of the glass substrate were polished by using zirconium abrasive grains (average particle size D50: 0.1, 0.2, 0.5, 0.7 μm) as an abrasive for evaluation. The zirconium abrasive grains have the same standard deviation SD (0.1 μm) as that of the zirconium abrasive grains used for polishing in the practical example 6 while only the average particle size D50 was different from the practical example 6. In the evaluation, in either case where the average particle size D50 was 0.2 or 0.5 μm, the result was the same as that of the practical example 6. In other words, an arithmetic average roughness Ra and a Dub-off value of the principal face were better than the practical example 2. On the other hand, in a case where the average particle size D50 was 0.1 μm, the result was sufficient enough, however, the polishing rate was lowered and particular improvement was not found in the evaluation result compared to the practical example 2 when the average particle size D50 was 0.7 μm.

In addition, the same zirconium oxide abrasive grains as in the practical example 6 were used as an abrasive while only hardness of a polisher pad to be used was changed with respect to the practical example 6 (JIS-A hardness: 95), in order to polish the principal face of the glass substrate and evaluate. As a result, when the polisher pad having hardness of 90 in JIS-A hardness was used, the evaluation result was almost the same as in the practical example 6. However, when the polisher pad having hardness of 85 in JIS-A hardness was used, the Dub-off value was +7 nm, which is slightly greater than the case of the practical example 6.

Furthermore, another polishing step using cerium oxide abrasive grains is also preferably executed between the first polishing step using a zirconium abrasive and the second polishing step using colloidal silica abrasive grains. When cerium oxide abrasive grains are used as an abrasive, the edge shape is easy to be a ski jump shape, thereby the Dub-off value can be lowered. It should be noted that the polishing step using the cerium oxide abrasive grains is preferably executed before a chemically strengthening step in order to maintain a large amount of compression stress layer formed on the principal face of the glass substrate by means of the chemically strengthening step.

An intermediate polishing step using cerium oxide abrasive grains, a chemically strengthening step, and a final polishing step (a post polishing step) were executed in this order with respect to the glass substrate in the practical example 2. In the intermediate polishing step, a slurry prepared by mixing 10% by weight of cerium oxide abrasive grains having a particle size of 1.0 μm into water, was used to polish a principal face of the glass substrate under the conditions as follows. As a result, a Dub-off value of the glass substrate after executing the final polishing step using colloidal silica as polishing abrasive grains was less than or equal to 5 nm, which was a remarkably good result.

<Polishing Conditions>
Polisher pad: Suede pad made of formed polyurethane (JIS-A hardness: 85)
Polishing load: 100 g/cm$^2$
Platen rotational speed: 30 rpm
Removal stock (total of front and back surfaces): 30 μm
Polishing device: Device similar to the device used in the first polishing step Different types of glass substrates were fabricated to have varied fracture toughness values of glass respectively by adjusting each glass composition. Specifically, the fracture toughness values of the glass substrates were 0.2, 0.4, 0.5, 1.0, 1.5, and 2.0 [MPa·m$^{1/2}$], respectively. The glass substrates were used for the first polishing with respect to the principal faces of the glass substrates. The polishing was executed under the same condition as in the practical example 2. The fracture toughness value was measured with a Vickers hardness tester.

When the glass substrates having the fracture toughness value of 0.2 and 2.0 [MPa·m$^{1/2}$] respectively were used, the polishing rate and existence of nano pits and/or nano scratches were almost the same degree as in the practical example 2. The degree of the polishing rate and existence of nano pits and/or nano scratches was higher than that of the practical example 2 when the fracture toughness value was 0.4 or 1.5 [MPa·m$^{1/2}$]. Moreover, the degree of the polishing rate and existence of nano pits and/or nano scratches was even higher when the fracture toughness value was 0.5 or 1.0 [MPa·m$^{1/2}$].

A magnetic disk was fabricated by forming a magnetic layer on a glass substrate for a magnetic disk obtained in the practical examples 1 to 6. Subsequently, the magnetic disk was assembled to a hard disk drive (HDD) having a rotational speed of 7200 rpm. Then, a certify test (recording/reproducing test of magnetic signal) was conducted while a DFH mechanism of a head was employed with the HDD. As a result of the test, an error was not occurred.

(5-2) Comparative Example and Practical Examples Represented in Table 2

In Table 2, an abrasive of a comparative example was fabricated by fracturing zirconia not containing a stabilizing agent. On the other hand, abrasives of practical examples are yttrium-contained zirconia, and the contained amount of yttrium is expressed by mole ratio (a ratio of $Y_2O_3$ with respect to ($Y_2O_3+ZrO_2$)) where yttrium is converted at yttria ($Y_2O_3$).

In the comparative example and the practical examples, average (D50) and standard deviation (SD) of the particle sizes of abrasive grains of an abrasive were approximately matched. Specifically, the average (D50) of the particle sizes was set to be in a range of 0.2 to 0.5 [μm], while the standard deviation (SD) was set to be in a range of 0.05 to 0.15 [μm]. More specifically, the average particle size (D50) was set to be 0.3 [μm], while the standard deviation (SD) was set to be 0.1 [μm]. The average (D50) and the standard deviation (SD) of the particle sizes of abrasive grains of the abrasive were measured using a particle size and particle size distribution measuring instrument (Nanotrac UPA-EX150 manufactured by NIKKISO CO., LTD.) by means of a light scattering method. In order to produce the slurry used in the polishing step, either reserve osmosis water (RO water) or pure water was mixed with the abrasives of the practical example and the comparative examples so as to be 10% by weight with respect to the reserve osmosis water or pure water and the mixture was sufficiently stirred. Subsequently, the glass substrate was polished by the polisher device while the slurries, containing abrasives of the practical example and the comparative examples, were respectively supplied thereto at a flow rate of 1 to 5 L/min. Here, the flow rate was set to be 3 L/min. The polishing conditions were as follows.

<Polishing Conditions>
Polisher pad: hard urethane foam pad (JIS-A hardness: 95)
Impregnated abrasive grain: cerium oxide
Average particle size of impregnated abrasive grain: 1 to 2 μm
Impregnation amount: 30% by weight
Polishing load: 100 g/cm$^2$
Platen rotational speed: 30 rpm

TABLE 2

| | Abrasive | | Evaluation Items | | |
|---|---|---|---|---|---|
| | Types of Zirconia | Ratio of $Y_2O_3$ by Mole | Polishing Speed | Flaw | End Shape |
| Comparative Example 3 | Zirconia | 0% | Good | Poor | Poor |
| Practical Example 7 | Yttrium-Contained Zirconia | 1% | Good | Good | Good |
| Practical Example 8 | Yttrium-Contained Zirconia | 3% | Excellent | Excellent | Excellent |
| Practical Example 9 | Yttrium-Contained Zirconia | 6% | Good | Good | Good |
| Practical Example 10 | Yttrium-Contained Zirconia | 8% | Good | Fair | Good |

The glass substrates, polished using the slurries containing the abrasives of the comparative example and the practical examples in Table 2, were respectively evaluated with three evaluation items of "Polishing Speed", "Flaw" and "Edge Shape". It should be noted that "Excellent", "Good" and "Fair" indicate an evaluation result evaluated as "Pass", whereas "Poor" indicates an evaluation result evaluated as "Fail".

"Polishing speed" as an evaluation item is an indicator for evaluating productivity in polishing and indicates that the faster the better. The plate thickness of the glass substrate was measured before and after polishing and the polishing speed was calculated by dividing the reduction amount of the plate thickness by a processing time. The polishing speed was evaluated based on the following evaluation criteria.

(Evaluation Criteria for Polishing Speed)
Excellent: >0.50 μm/min
Good: 0.40 to 0.50 μm/min
Fair: 0.30 to 0.40 μm/min
Poor: <0.30 μm/min "Flaw" as an evaluation item is an indicator for evaluating the surface quality of the principal faces of the glass substrate. A visual inspection was conducted for the principal faces of the magnetic disk glass substrate under a halogen focus lamp, and it was determined whether or not a flaw such as a pit or a scratch (with a depth of 250 nm or greater) exists. The inspection was conducted for 200 post-polishing substrates regarding each comparative or practical example. A substrate, having even a single flaw on the principal face thereof, was evaluated as failed, and a passed ratio (non-defective ratio) of 200 substrates was evaluated based on the following evaluation criteria.

(Evaluation Criteria for Flaw)
Excellent: 95 to 100%
Good: 90 to 95%
Fair: 80 to 90%
Poor: <80%

Figure 3A:
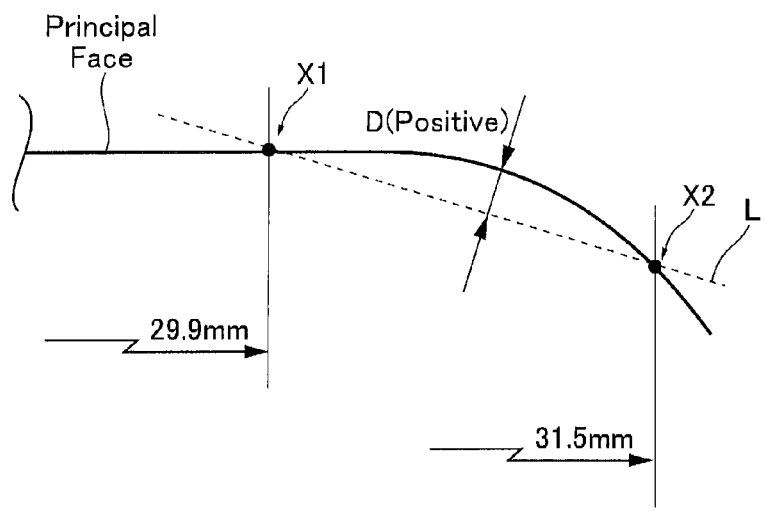
FIGS. 3A and 3B include diagrams for conceptually explaining a method of calculating a dub-off value of the edge shape of a glass substrate.
Figure 3B:
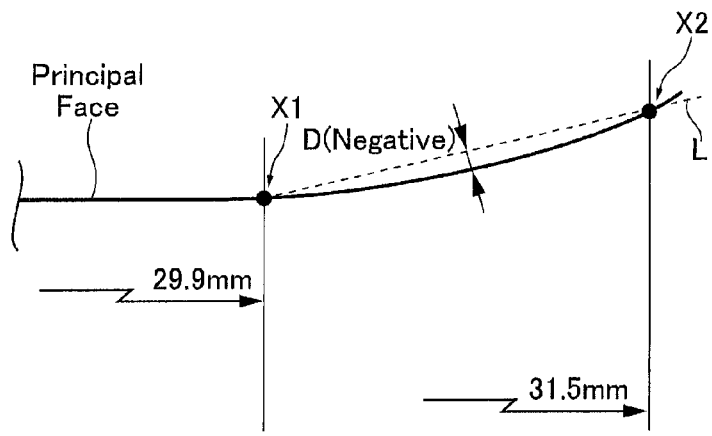

Dub-off values were evaluated for evaluating the edge shape. FIGS. 3A and 3B are diagrams of an enlarged cross-section of an edge of the glass substrate for conceptually explaining a method of calculating a dub-off value. To calculate a dub-off value, the center point of the glass substrate, X1 and X2 are defined as illustrated in FIGS. 3A and 3B (wherein a glass substrate has an outer diameter of 65 mm). Here, X1 is a position located away from the center point at a distance of 30 mm or 29.9 mm towards the outer edge on a principal face, while X2 is a position located away from the center point at a distance of 31.5 mm towards the outer edge on the principal face. It should be noted that, seen from the above of the glass substrate, the center point, X1 and X2 of the glass substrate are located on the same line. When the principal face is herein protruded with respect to a base line L connecting X1 and X2, the edge of the glass substrate has a roll-off shape (in the case of in FIG. 3A) and the maximally protruded amount is set as a dub-off value D (a positive value). By contrast, when the principal face is recessed with respect to the base line L connecting X1 and X2, the edge of the glass substrate has a ski jump shape (in the case of in FIG. 3B) and the maximally recessed amount is set as a dub-off value D (a negative value). A profilometer (MicroXAM manufactured by Phase Shift Corporation) was used for measuring a dub-off value.

A dub-off value for a single annular glass substrate is calculated as follows. Dub-off values are calculated for four points (four pairs of X1 and X2) at 90 degree intervals with respect to one of the principal faces. Amongst four dub-off values herein calculated, the one with the largest absolute value is set as a dub-off value for the principal face (which is either a positive value or a negative value). Similarly, a dub-off value is calculated for the other of the principal faces. Then, the average of the dub-off values of the both principal faces is set as a dub-off value for the glass substrate (which is either a positive value or a negative value). The obtained dub-off value of the glass substrate was evaluated based on the following evaluation criteria.

It should be noted that the following evaluation criteria are not for a final product but for a glass substrate having experienced the first polishing step. In the final product, the edge shape will be further better through the post polishing step (second polishing step).

(Evaluation Criteria for Edge Shape)
Excellent: <17.0 nm
Good: 17.0 to 19.0 nm
Fair: 19.0 to 21.0 nm
Poor: >21.0 nm As is obvious from Table 2, the cases using the abrasives made of yttrium-contained zirconia show better results for all the evaluation items, compared to the case using the abrasive made of zirconia abrasive grains. Moreover, a further better result was obtained when the contained amount of yttria in yttrium-contained zirconia is in a range of 1 to 6% (by mole).

It should be noted that it was confirmed that, regarding the practical examples 7 to 9, the removal stock was less than or equal to 5 µm in the second polishing step and the surface asperity and the edge shape of the principal face of the glass substrate were good.

Figure 4:
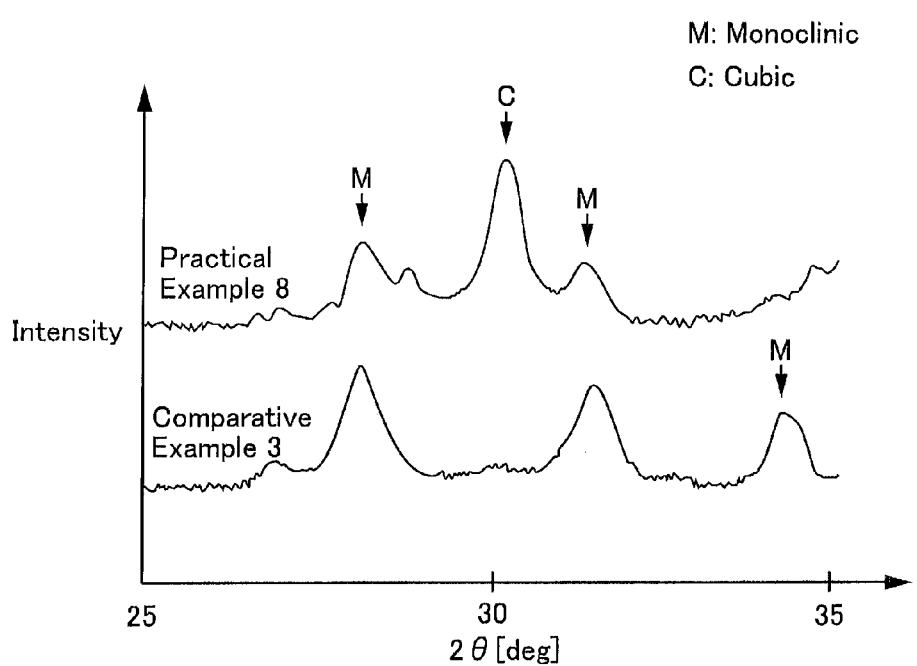
FIG. 4 is a chart for representing measurement results by an x-ray powder diffraction device regarding abrasives of practical examples.

FIG. 4 represents measurement results for the abrasives of the aforementioned comparative example 3 and practical example 8 by an x-ray powder diffraction device (SmartLab System 9 KW manufactured by Rigaku Corporation). It should be noted that in FIG. 4, the vertical axis indicates diffraction intensity (Intensity) of an arbitrary unit expressed by common logarithm while the horizontal axis indicates 2θ, and further, the measurement result of the comparative example 3 and that of the practical example 8 are herein shifted without being overlapped.

As represented in FIG. 4, in the measurement result of the comparative example 3, strong peak intensities (diffraction intensities) were confirmed at the vicinity of 28.1 [deg], 31.4 [deg] and 34.2 [deg]. The peak intensities can be considered as diffraction peaks attributed to zirconia having the monoclinic crystalline structures. In the measurement result of the practical example 8, on the other hand, a strong peak intensity was also confirmed at the vicinity of 30.2 [deg] in addition to the diffraction peaks that could be attributed to zirconia of the monoclinic crystalline structures. The peak intensity can be considered as a diffraction peak attributed to zirconia having the cubical crystalline structures, and is higher than a peak intensity originated from the monoclinic crystalline structures. In short, it can be understood that in the practical example 8, the peak of the diffraction intensity of the cubic crystalline structures is the highest in the peaks of the diffraction intensities of the crystalline structures of zirconia. From the measurement results of FIG. 4, it can be considered that the crystalline structures of the zirconia abrasives of the comparative example 3 and the practical example 8 are greatly different from each other.

Furthermore, yttrium-contained zirconia which has the same average particle size and standard deviation as in the case of practical example 8 and whose yttrium content (mole ratio of $Y_2O_3$) is in a range of 2 to 5%, was used as an abrasive. The evaluation result was good as in the practical example 8 (yttrium content: 3%). Accordingly, it is found that yttrium content set in a range of 2 to 5% brings remarkably good results.

Dub-off value of less than or equal to 21 nm is evaluated as "Pass" as evaluation criteria of edge shape with reference to Table 2. However, in a case employing severer evaluation criteria (for example, Dub-off value of less than or equal to 10 nm is evaluated as "Pass"), another polishing step is preferably executed by using cerium oxide abrasive grains between the first polishing step using a zirconium abrasive and the second polishing step using colloidal silica abrasive grains. When cerium oxide abrasive grains are used as an abrasive, the edge shape is easy to be a ski jump shape, thereby the Dub-off value can be lowered. It should be noted that the polishing step using the cerium oxide abrasive grains is preferably executed before a chemically strengthening step in order to maintain a large amount of compression stress layer formed on the principal face of the glass substrate by means of the chemically strengthening step.

An intermediate polishing step using cerium oxide abrasive grains, a chemically strengthening step, and a final polishing step (a post polishing step) were executed in this order with respect to the glass substrate in the practical example 8. In the intermediate polishing step, a slurry prepared by mixing 10% by weight of cerium oxide abrasive grains having a particle size of 1.0 µm into water, was used to polish a principal face of the glass substrate under the conditions as follows. As a result, a Dub-off value of the glass substrate after executing the final polishing step using colloidal silica as polishing abrasive grains was less than or equal to 5 nm, which is a remarkably good result.

<Polishing Conditions>
Polisher pad: Suede pad made of formed polyurethane (JIS-A hardness: 85)
Polishing load: 100 g/cm2
Platen rotational speed: 30 rpm
Removal stock (total of front and back surfaces): 30 µm
Polishing device: Device similar to the device used in the first polishing step Different types of glass substrates were fabricated to have varied fracture toughness values of glass respectively by adjusting each glass composition. Specifically, the fracture toughness values of the glass substrates are 0.2, 0.4, 0.5, 1.0, 1.5, and 2.0 [MPa·m1/2], respectively. The glass substrates were used for the first polishing with respect to the principal faces of the glass substrates. The polishing was executed under the same condition as in the practical example 8. The fracture toughness value was measured with a Vickers hardness tester.

When the glass substrates having the fracture toughness value of 0.2 and 2.0 [MPa·m$^{1/2}$] respectively were used, the polishing speed, flaws, and an edge shape were almost the same degree as in the practical example 2. The degree of the polishing speed, flaws, and an edge shape was higher than that of the practical example 8 when the fracture toughness value was 0.4 or 1.5 [MPa·m$^{1/2}$]. Moreover, the degree the polishing speed, flaws, and an edge shape was even higher when the fracture toughness value was 0.5 or 1.0 [MPa·m$^{1/2}$].

A magnetic disk was fabricated to have a magnetic layer formed on a glass substrate for a magnetic disk which was obtained in the practical examples 7 to 10. Subsequently, the magnetic disk was assembled to a hard disk drive (HDD) having a rotational speed of 7200 rpm. Then, a certify test (recording/reproducing test of magnetic signal) was conducted while a DPH mechanism of a head was employed with the HDD. As a result of the test, an error was not occurred.

A manufacturing method of a glass substrate for a magnetic disk of the present invention has been explained above in detail. However, the present invention is not limited to the aforementioned exemplary embodiment, and it is apparent that a variety of modifications and changes can be made without departing from the scope of the present invention.

REFERENCE SIGNS LIST

10 Polisher Pad
30 Carrier
40 Top platen
50 Bottom platen
61 Sun gear
62 Internal gear
71 Slurry supply tank
72 Pipe
100 Primary particles
200 Aggregate
M Monoclinic crystalline structure
T Tetragonal crystalline structure

What is claimed is:

1. A manufacturing method of a glass substrate for a magnetic disk, comprising:
polishing a principal face of the glass substrate using a slurry containing zirconium oxide abrasive grains, each of the abrasive grains having zirconium oxide as a principal component, with the zirconium oxide in each of the abrasive grains having crystallites of monoclinic crystalline structures and crystallites of tetragonal crystalline structures as an abrasive, and in each of the zirconium oxide abrasive grains, a ratio of the amount of the tetragonal crystalline structures with respect to the amount of the monoclinic crystalline structures falls in a range of 0.7% to 3.0%, where the ratio is obtained by x-ray diffraction and is defined as a ratio of a peak intensity of the tetragonal crystalline structures with respect to a peak intensity of the monoclinic crystalline structures, and the peak intensity is defined as an integrated peak intensity.

2. The manufacturing method of a glass substrate for a recited in claim 1, wherein the zirconium oxide abrasive grains are made of aggregates of primary particles of zirconium oxide and the primary particles of zirconium oxide have crystallites of the monoclinic crystalline structures and crystallites of the tetragonal crystalline structures.

3. The manufacturing method of a glass substrate for a magnetic disk recited in claim 1, wherein the zirconium oxide abrasive grains do not contain stabilizing agent.

4. The manufacturing method of a glass substrate for a magnetic disk recited in claim 1, wherein the average particle size D50 of the zirconium oxide abrasive grains is set to be in a range of 0.2 to 0.5 μm.

5. The manufacturing method of a glass substrate for a magnetic disk recited in claim 1, wherein a polisher pad is used for polishing a principal face of the glass substrate in the polishing, the polisher pad having hardness in a range of 80 to 100 in JIS-A hardness.

6. The manufacturing method of a glass substrate for a magnetic disk recited in claim 1, wherein the glass substrate is made of glass, the glass having the fracture toughness value in a range of 0.4 to 1.5 $MPa \cdot m^{1/2}$.

7. The manufacturing method of a glass substrate for a magnetic disk recited in claim 1, further comprising:
after the polishing, performing a post polishing using a slurry containing colloidal silica as abrasive grains.

8. The manufacturing method of a glass substrate for a magnetic disk recited in claim 7, wherein a removal stock is set to be less than or equal to 5 μm in the post polishing.

9. The manufacturing method of a glass substrate for a magnetic disk recited in claim 7, further comprising:
an intermediate polishing using a slurry containing cerium oxide abrasive grains, the intermediate polishing being performed between the polishing and the post polishing.

10. The manufacturing method of a glass substrate for a magnetic disk recited in claim 7, further comprising:
a chemically strengthening process performed between the polishing and the post polishing.

11. A magnetic disk made of a glass substrate manufactured with the method recited in claim 1, wherein at least a magnetic layer is formed on a principal face of the glass substrate.

12. A magnetic recording/reproducing device, comprising:
the magnetic disk recited in claim 11; and
a magnetic head embedded with a DFH (Dynamic Flying Height) control mechanism.

13. The manufacturing method of a glass substrate for a magnetic disk recited in claim 1, wherein the zirconium oxide abrasive grains are obtained by sintering zirconium oxide formed by the monoclinic crystalline structures substantially at a temperature that begins phase transition from the monoclinic crystalline structures to the tetragonal crystalline structures.

* * * * *